(12) United States Patent
Eder et al.

(10) Patent No.: US 6,488,637 B1
(45) Date of Patent: Dec. 3, 2002

(54) COMPOSITE ENDOVASCULAR GUIDEWIRE

(75) Inventors: Joseph Eder, Los Altos, CA (US); Christopher G. M. Ken, San Mateo, CA (US); Roger Farnholtz, Fremont, CA (US)

(73) Assignee: Target Therapeutics, Inc., Fremont, CA (US)

( * ) Notice: Subject to any disclaimer, the term of this patent is extended or adjusted under 35 U.S.C. 154(b) by 876 days.

(21) Appl. No.: 08/640,343

(22) Filed: Apr. 30, 1996

(51) Int. Cl.[7] .................................................. A61B 5/00
(52) U.S. Cl. ........................................................ 600/585
(58) Field of Search .................................. 128/772, 657, 128/658; 604/95, 280–282; 600/433–436, 585

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 3,753,700 A | 8/1973 | Harrison et al. |
| 3,789,841 A | 2/1974 | Antoshkiw |
| 4,545,390 A | 10/1985 | Leary |
| 4,619,274 A | 10/1986 | Morrison |
| 4,665,906 A | 5/1987 | Jervis |
| 4,719,924 A | 1/1988 | Crittenden et al. |
| 4,739,768 A | 4/1988 | Engelson |
| 4,884,579 A | 12/1989 | Engelson ..................... 128/772 |
| 4,925,445 A | 5/1990 | Sakamoto et al. |
| 4,966,163 A | 10/1990 | Kraus et al. |
| 4,969,890 A | 11/1990 | Sugita et al. |
| 4,984,581 A | 1/1991 | Stice |
| 4,991,602 A | 2/1991 | Amplatz et al. |
| 5,069,226 A | 12/1991 | Yamauchi et al. |
| 5,095,915 A | 3/1992 | Engelson |
| 5,171,383 A | 12/1992 | Sagaye et al. |
| 5,213,111 A | 5/1993 | Cook et al. |
| 5,230,348 A | 7/1993 | Ishibe et al. |
| 5,239,004 A | 8/1993 | Sahatjian et al. |
| 5,243,996 A | 9/1993 | Hall |
| 5,303,714 A | 4/1994 | Abele et al. |
| RE34,695 E | 8/1994 | Mar et al. |
| 5,341,818 A | 8/1994 | Abrams et al. |
| 5,365,943 A | 11/1994 | Jansen ......................... 128/772 |
| 5,368,049 A | 11/1994 | Raman et al. |
| 5,385,152 A | 1/1995 | Abele et al. |
| 5,402,799 A | 4/1995 | Colon et al. |
| 5,411,476 A | 5/1995 | Abrams et al. |
| 5,443,907 A | 8/1995 | Slaikeu et al. |
| 5,452,726 A | 9/1995 | Burmeister et al. |
| 5,465,733 A | 11/1995 | Hinohara et al. |
| 5,496,275 A | 3/1996 | Sirhan et al. |
| 5,505,725 A | 4/1996 | Samson ......................... 606/7 |
| 5,533,985 A | * 7/1996 | Wang ......................... 604/264 |

FOREIGN PATENT DOCUMENTS

| | | |
|---|---|---|
| EP | 0376132 | 7/1990 |
| EP | 0395098 | 10/1990 |
| EP | 0436303 | 7/1991 |
| EP | 0491349 | 6/1992 |
| EP | 0515201 | 11/1992 |
| EP | 0519604 | 12/1992 |
| EP | 0661073 | 7/1995 |
| JP | 4-9162 | 1/1992 |
| WO | WO 91/15152 | 10/1991 |

* cited by examiner

*Primary Examiner*—Max Hindenburg
(74) *Attorney, Agent, or Firm*—Crompton, Seager & Tufte, LLC

(57) ABSTRACT

This invention is a surgical device. It is a composite guidewire for use in a catheter and is used for accessing a targeted site in a lumen system of a patient's body. The composite guidewire assembly is especially useful for accessing peripheral or soft tissue targets. The invention includes multi-section guidewire assemblies having (at least) super-elastic distal portions and super-elastic braided reinforcements along the mid or distal sections. A variation of the inventive guidewire includes the coating of the wire with a tie layer and then with a one or more lubricious polymers to enhance its suitability for use within catheters and with the interior of vascular lumen.

14 Claims, 2 Drawing Sheets

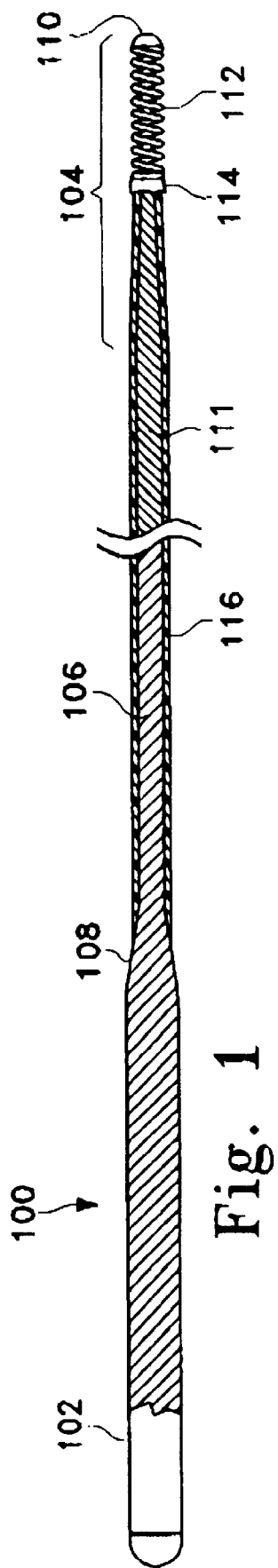
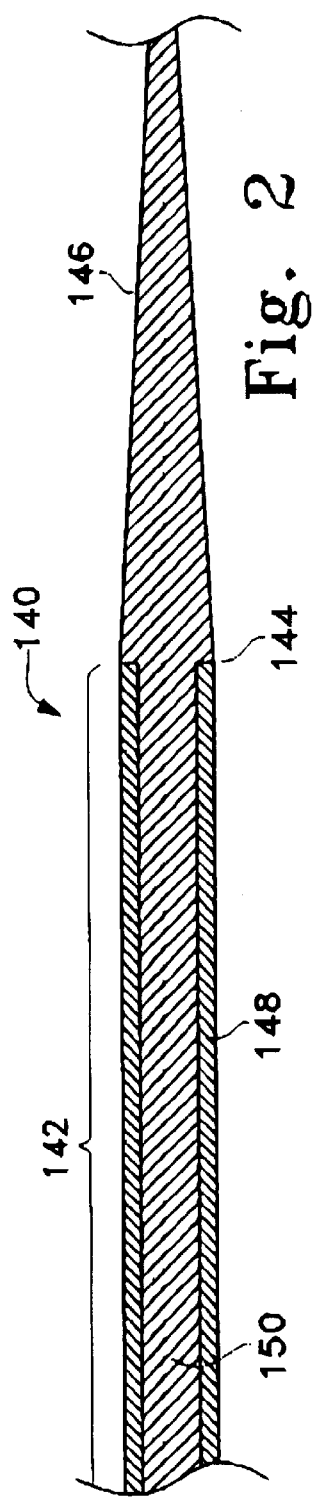
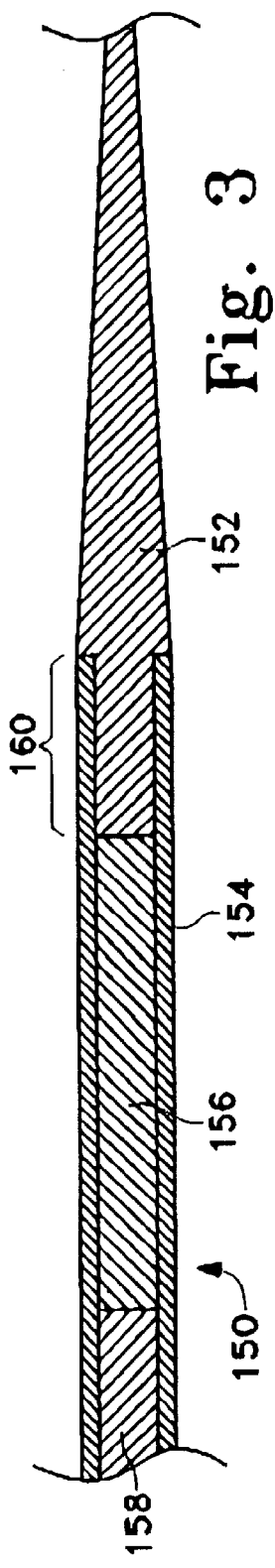
Fig. 1
Fig. 2
Fig. 3

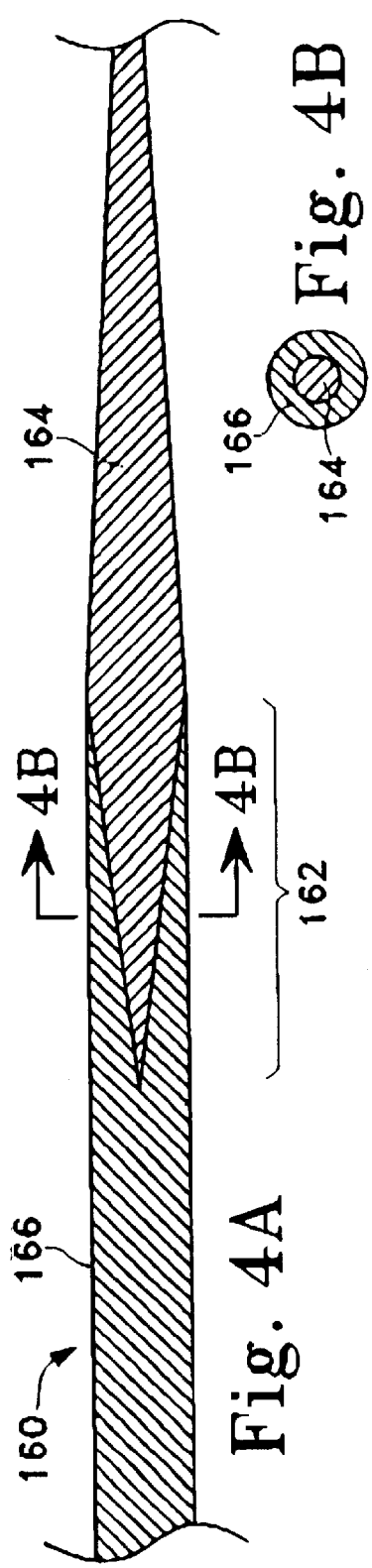
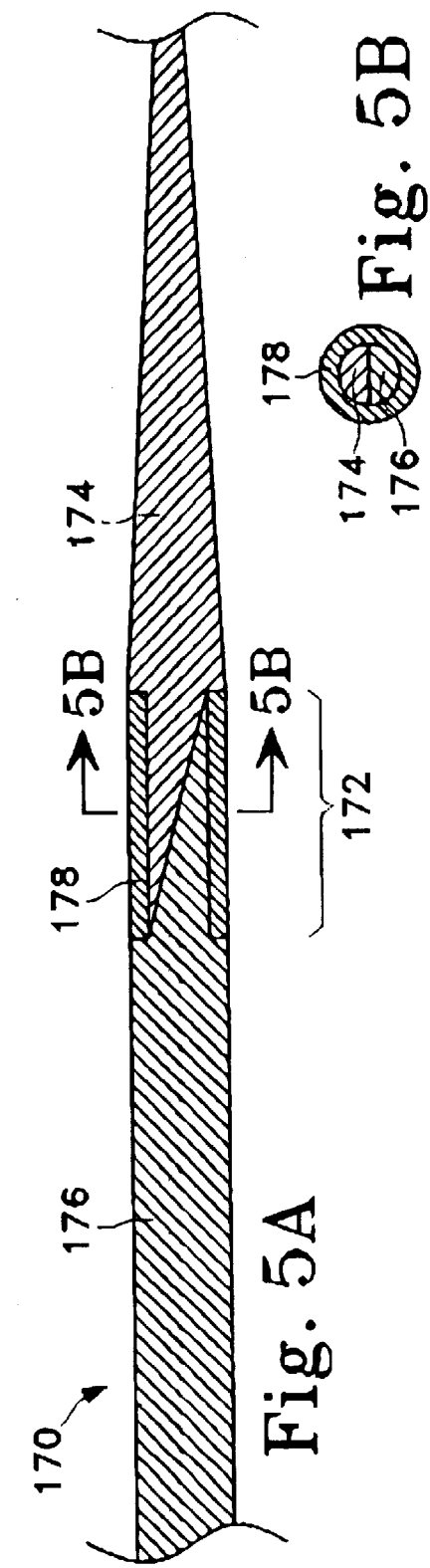
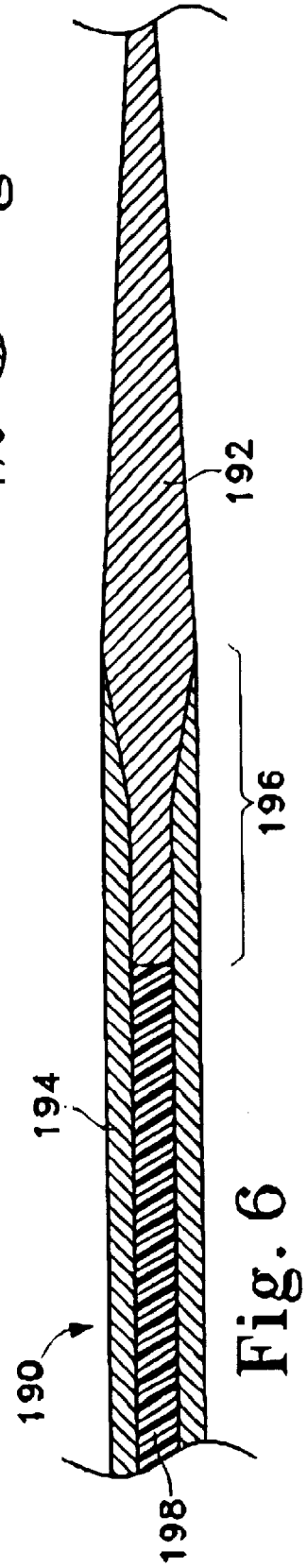

COMPOSITE ENDOVASCULAR GUIDEWIRE

FIELD OF THE INVENTION

This invention is a surgical device. It is a composite guidewire for use in a catheter and is used for accessing a targeted site in a lumen system of a patient's body. The composite guidewire assembly is especially useful for accessing peripheral or soft tissue targets. The invention includes multi-section guidewire assemblies having (at least) super-elastic distal portions. The mid-section joining the distal section to the proximal section preferably has varying stiffness. The guidewire may have a composite proximal section made by swaging or pulling the composite section through a die to join the outer layer to the inner core. A variation of the inventive guidewire includes the coating of the wire with a tie layer and then with a one or more lubricious polymers to enhance its suitability for use within catheters and with the interior of vascular lumen.

BACKGROUND OF THE INVENTION

Catheters are used increasingly as a means for delivering diagnostic and therapeutic agents to internal sites within the human body that can be accessed through various of the body's lumen systems, particularly through the vasculature. A catheter guidewire is used for guiding the catheter through the bends, loops, and branches forming the blood vessels within the body. One method of using a guidewire to direct the catheter through the torturous paths of these systems of lumen involves the use of a torqueable guidewire which is directed as a unit from a body access point such as the femoral artery to the tissue region containing the target site. The guidewire is typically bent at its distal end, and may be guided by alternately rotating and advancing the guidewire along the small vessel pathway to the desired target. The guidewire and the catheter are advanced by alternately moving the guidewire along a distance in the vessel pathway, holding the guidewire in place, and then advancing the catheter along the axis of the guidewire until it reaches the portion of the guidewire already advanced farther into the human body.

The difficulty in accessing remote body regions, the body's periphery or the soft tissues within the body such as the brain and the liver, are apparent. The catheter and its attendant guidewire must both be flexible, to allow the combination to follow the complicated path through the tissue, and yet stiff enough to allow the distal end of the catheter to be manipulated by the physician from the external access site. It is common that the catheter is as long as a meter or more.

The catheter guidewires used in guiding a catheter through the human vasculature have a number of variable flexibility constructions. For instance, U.S. Pat. Nos. 3,789,841; 4,545,390; and 4,619,274 show guidewires in which the distal end section of the wire is tapered along its length to allow great flexibility in that remote region of the guidewire. This is so, since the distal region is where the sharpest turns are encountered. The tapered section of the wire is often enclosed in a wire coil, typically a platinum coil, to increase the column strength of the tapered wire section without significant loss of flexibility in that region and also to increase the radial capacity of the guidewire to allow fine manipulation of the guidewire through the vasculature.

Another effective guidewire design is found in U.S. Pat. No. 5,095,915. This patent shows a guidewire having at least two sections. The distal portion is encased in an elongated polymer sleeve having axially spaced grooves to allow increased bending flexibility of the sleeve.

Others have suggested the use of guidewires made of various super-elastic alloys in an attempt to achieve some of the noted functional desires.

U.S. Pat. No. 4,925,445, to Sakamoto et al., suggests the use of a two-portion guidewire having a body portion relatively high in rigidity and a distal end portion which is comparatively flexible. At least one portion of the body and the distal end portions is formed of super-elastic metallic materials. Although a number of materials are suggested, including Ni—Ti alloys of 49 to 58% (atm) nickel, the patent expresses a strong preference for Ni—Ti alloys in which the transformation between austentite and martensite is complete at a temperature of 10° C. or below. The reason given is that "for the guidewire to be useable in the human body, it must be in the range of 10° to 20° C. due to anesthesia at a low body temperature." The temperature of the human body is typically about 37° C.

Another document disclosing a guidewire using a metal alloy having the same composition as a Ni—Ti super-elastic alloy is WO91/1512 (to Sahatjian et al. and owned by Boston Scientific Corp.). That disclosure suggests a guidewire made of the precursor to the Ni—Ti elastic alloy. Super-elastic alloys of this type are typically made by drawing an ingot of the precursor alloy while simultaneously heating it. In the unstressed state at room temperature, such super-elastic materials occur in the austenite crystalline phase and, upon application of stress, exhibit stress-induced austenite-martensite (SIM) crystalline transformations which produce nonlinear elastic behavior. The guidewires described in that published application, on the other hand, are said not to undergo heating during the drawing process. The wires are cold-drawn and great pain is taken to assure that the alloy is maintained well below 3000 F. during each of the stages of its manufacture. This temperature control is maintained during the step of grinding the guidewire to form various of its tapered sections.

U.S. Pat. No. 4,665,906 suggests the use of stress-induced martensite (SIM) alloys as constituents in a variety of different medical devices. Such devices are said to include catheters and cannulas.

U.S. Pat. No. 4,969,890 to Sugita et al., suggests the production of a catheter having a main body fitted with a shape memory alloy member, and having a liquid injection means to supply a warming liquid to allow the shape memory alloy member to recover its original shape upon being warmed by the fluid.

U.S. Pat. No. 4,984,581, to Stice, suggests a guidewire having a core of a shape memory alloy, the guidewire using the two-way memory properties of the alloy to provide both tip-deflecting and rotational movement to the guidewire in response to a controlled thermal stimulus. The controlled thermal stimulus in this instance is provided through application of an RF alternating current. The alloy selected is one that has a transition temperature between 36° C. and 45° C. The temperature 36° C. is chosen because of the temperature of the human body; 45° C. is chosen because operating at higher temperatures could be destructive to body tissue, particularly some body proteins.

U.S. Pat. No. 4,991,602 to Amplatz et al., suggests a flexible guidewire made up of a shape memory alloy such as the nickel-titanium alloy known as nitinol. The guidewire is one having a single diameter throughout its midcourse, is tapered toward each end, and has a bead or ball at each of those ends. The bead or ball is selected to allow ease of movement through the catheter into the vasculature. The guidewire is symmetrical so that a physician cannot make a wrong choice in determining which end of the guidewire to insert into the catheter. The patent suggests that wound wire coils at the guidewire tip are undesirable. The patent further suggests the use of a polymeric coating (PTFE) and an anticoagulant. The patent does not suggest that any particular type of shape memory alloy or particular chemical or physical variations of these alloys are in any manner advantageous.

Another catheter guidewire using Ni—Ti alloys is described in U.S. Pat. No. 5,069,226, to Yamauchi, et al. Yamauchi et al. describes a catheter guidewire using a Ni—Ti alloy which additionally contains some iron, but is typically heat-treated at a temperature of about 400° to 500° C. so as to provide an end section which exhibits pseudo-elasticity at a temperature of about 37° C. and plasticity at a temperature below about 80° C. A variation is that only the end portion is plastic at the temperatures below 80° C.

U.S. Pat. No. 5,171,383, to Sagae, et al., shows a guidewire produced from a super-elastic alloy which is then subjected to a heat treatment such that the flexibility is sequentially increased from its proximal portion to its distal end portions. A thermoplastic coating or coil spring may be placed on the distal portion of the wire material. Generally speaking, the proximal end portion of the guidewire maintains a comparatively high rigidity and the most distal end portion is very flexible. The proximal end section is said in the claims to have a yield stress of approximately five to seven kg/mm$^2$ and an intermediate portion of the guidewire is shown in the claims to have a yield stress of approximately 11 to 12 kg/mm$^2$.

Published European Patent Application 0,515,201-A1 also discloses a guidewire produced at least in part of a super-elastic alloy. The publication describes a guidewire in which the most distal portion can be bent or curved into a desired shape by a physician immediately prior to use in a surgical procedure. Proximal of the guide tip, the guidewire is of a super-elastic alloy. Although nickel-titanium alloys are said to be most desirable of the class shown in that disclosure, no particular physical description of those alloys is disclosed to be any more desirable than another.[22]

Published European Patent Application 0,519,604-A2 similarly discloses a guidewire which may be produced from a super-elastic material such as nitinol. The guidewire core is coated with a plastic jacket, a portion of which may be hydrophilic and a portion of which is not.

Examples of Ni—Ti alloys are disclosed in U.S. Pat. Nos. 3,174,851; 3,351,463; and 3,753,700.

We have found that in certain instances, the use of superelastic alloys gives a guidewire which is insufficiently stiff in the proximal region and which does not transmit torque in a desirable fashion.

Our solution is to provide a composite guidewire having a stiff proximal section with exceptional torque-transmitting capabilities and a more distal section with the flexibility and super-elasticity inherent to the super-elastic alloys.

U.S. Pat. No. 5,411,476, to Abrams, shows a composite guidewire having, apparently, a portion of a super elastic alloy as seen in FIG. 1. The step joint is shown merging the distal and proximal sections of the device there.

U.S. Pat. No. 5,303,714, to Abele et al. and its relative U.S. Pat. No. 5,385,152, each show a guidewire used for crossing occlusions in blood vessels. That is to say that it is a guidewire and is used to press through an occlusion found in an artery. This use requires, in that invention, the presence of an enlarged distal portion (24 in the figures) having a lubricious outer surface. The guidewires are said in some instances, (see FIGS. 8 and 9 and the related explanation) to have a wire made out of internal member of a super elastic alloy such as nitinol and an outer sleeve member such as a thin-walled hypodermic tube.

Japanese Kokai 4-9162, owned by the Terumo Corporation of Japan, shows a two-section guidewire. The more distal section is made up of nickel/titanium alloy and the proximal is a highly rigid stainless steel. The joint between two is seen to be a butt joint.

U.S. Pat. No. 5,341,818, to Abrams et al, shows a guidewire having a distal portion formed of a super elastic alloy. The proximal section is said to be "high strength" and is joined to the distal super elastic alloy portion using a connector element 13.

U.S. Pat. No. 5,213,111, to Cook et al, shows a guidewire construction made up of a coaxial composite of a thin stainless steel wire surrounded by a shape memory alloy such as one comprising nickel/titanium. The complete guidewire is encoated with a polymer and at least the distal 70–80% of it is coated with a hydrophilic polymer to increase the lubricity.

None of these disclosures suggest the guidewire configuration described below.

SUMMARY OF THE INVENTION

This invention is a guidewire, preferably a guidewire suitable for introduction into the vasculature of the brain, and a method for its use. At least a distal portion of the guidewire may be of a super-elastic alloy which preferably is a Ni—Ti alloy.

A highly desirable variation of the inventive guidewire comprises a long wire having a proximal section, an intermediate section, and a distal section. The distal end section is typically the most flexible of the sections and is at least about three centimeters long. Desirably, the flexible distal end section is partially tapered and is covered by a coil assembly which is connected to the distal end of the guidewire at its distal tip. The coil assembly may be attached to the distal tip by soldering, perhaps after plating or coating the distal end section with a malleable or solderable metal, such as gold.

The guidewire, whether of a super-elastic metal or not, may be coated with a polymer or other material to enhance its ability to traverse the lumen of the catheter. A lubricious polymer may be placed directly upon the core wire or upon a "tie" layer. The tie layer may be a shrink-wrap tubing or a plasma deposition or may be a dip, spray, or fusion spray coating of an appropriate material. The tie layer may also be radio opaque.

The guidewire of this invention may be of a composite in which a distal portion of the core is a super-elastic alloy and the more proximal section or sections are of another material or configuration, e.g., stainless steel wire or rod, stainless steel hypotube, super-elastic alloy tubing, carbon fiber tubing, etc.

The proximal portion may also be a composite itself. The inner core may be a stainless steel, super-elastic alloy, or a polymeric composition. The outer covering is of a different composition and may be a stainless steel or super-elastic alloy. The joint between the proximal and distal sections may be of a special configuration to provide, ideally, a smooth transition in flexibility between the two sections.

Ideally there will be one or more radiopaque markers placed upon the guidewire, e.g., at its distal tip and potentially along the length of the intermediate section. These markers may be used both to enhance the guidewire's radiopacity and its ability to transmit torque from the proximal end to the distal end while maintaining a desired flexibility.

This invention also may also include a catheter apparatus made up of the guidewire core and a thin-walled catheter designed to be advanced along the guidewire through the vasculature for positioning at a desired site.

BRIEF DESCRIPTION OF THE DRAWINGS

FIG. 1 shows a schematic side view (not to scale) of the major components of the inventive guidewire.

FIG. 2 is a partial cutaway, side view of a first variation of a composite guidewire made according to this invention having a distal portion of a highly elastic alloy.

FIG. 3 is a partial cutaway, side view of a second variation of a composite guidewire made according to this invention having a distal portion of a highly elastic alloy.

FIG. 4A is a partial cutaway, side view of a third variation of a composite guidewire made according to this invention having a distal portion of a highly elastic alloy.

FIG. 4B is a cross-section of the guidewire of FIG. 4A.

FIG. 5A is a partial cutaway, side view of a fourth variation of a composite guidewire made according to this invention having a distal portion of a highly elastic alloy.

FIG. 5B is a cross-section of the guidewire of FIG. 5A.

FIG. 6 is a partial cutaway, side view of a fifth variation of a composite guidewire made according to this invention having a distal portion of a highly elastic alloy.

DESCRIPTION OF THE INVENTION

FIG. 1 shows an enlarged side view of a guidewire made according to the invention. The guidewire (100) is made up of the wire core formed of a flexible torqueable wire filament material, of the alloys described herein, and has a total length typically between about 50 and 300 centimeters. The proximal section (102) preferably has a uniform diameter (along its length) of about 0.010 to 0.025 inches, preferably 0.010 to 0.018 inches. The relatively more flexible distal section (104) extends for 3 to 30 centimeters or more of the distal end of the guidewire (100). There may be a middle section (106) having a diameter intermediate between the diameter of the two portions of the wire adjoining the middle section. The middle section (106) may be continuously tapered, may have a number of tapered sections or sections of differing diameters, or may be of a uniform diameter along its length. If middle section (106) is of a generally uniform diameter, the guidewire core will neck down as is seen at (108). The distal section (104) of the guidewire (100) typically has an end cap (110), a fine wire coil (112), and a solder joint (114). The fine wire coil (112) may be radiopaque and made from materials including but not limited to platinum and its alloys. Alternatively, the fine wire coil (112) may be made of superelastic alloys, such as those alloys comprising nickel and titanium, for example. The end cap (110) may be radiopaque to allow knowledge of the position of the coil (112) during the process of inserting the catheter and traversal of the guidewire through the vasculature. All or part of the guidewire proximal section (102) and middle section (106) and distal section (104) may be coated with a thin layer (116) of polymeric material to improve its lubricity without adversely affecting the flexibility or shapeability of the guidewire. This invention includes portions or sections of the guidewire described above having the noted polymeric tie layer described below and a slippery, e.g., a hydrophilic polymeric coating thereon.

FIG. 2 shows a variation of the inventive guidewire which is a composite, e.g., a distal portion of the guidewire core is produced of the specified alloy and the composite is of another material or configuration. In particular, the composite guidewire (140) is made up of a more proximal section (142) that is a section of small diameter tubing of an appropriate stainless steel or a high performance polymer such as a polyimide. Tubular composites such as superelastic alloy ribbon tubular braids having polymeric coverings and perhaps polymeric interiors are also desirable. The tubular proximal section (142) is attached by soldering or by gluing or by other joining method suitable for the materials involved at the joint (144) to a distal section (146) that extends to the distal end of the composite guidewire assembly. Most preferred in this variation is the use of a superelastic alloy which passes completely through the device, from proximal to distal end, and is passed through a die along with the outer tubing (148) to form a relatively integral assembly in which the inner portion (150) of the proximal section is intimately joined to the outer tubing (148).

FIG. 3 shows a partial cutaway of another embodiment of the inventive guidewire (150).

This variation of the invention involves a guidewire having multiple sections of varying flexibility. The most distal section (152) is preferably made of super elastic alloy as discussed elsewhere herein. The guidewire assembly (150) further has an outer covering (154) which is all the same materials as a covering (148) found in FIG. 2. The guidewire further has an interior insert (156) and a most proximal insert (158). For ease of assembly, these inserts (152 and 158) simply are placed inside the outer tubing (154) and joined to the outer tubing in such a fashion that the catheter assembly is able to transmit torque without torsional slippage between inner member (156) and outer tubing (154). Such joining may be done by welding, by application of glues, by swaging, or by pulling the entire assembly through an appropriately sized die. The construction in this form provides a sequence of varying flexibility. For instance, the most distal section (152) is the most flexible. Region (160) is typically the next most flexible. The region of the guidewire defined by inner member (156) is typically somewhat less stiff than is the most proximal section defined by the presence of inner member (158). By careful selection of the inner member (156) and (158), the appropriate flexibility torque transmission, and overall utility of the guidewire assembly (150) is easily defined.

FIG. 4A shows another variation of the inventive guidewire (160) in which the joint region between the distal section (164) and the more proximal section (166) is used both to join the proximal section (166) and the distal section (164) but also provides for steady transition in the region between those two sections. The joint in the mid-section (162) is a taper joint. The two sections are joined typically by metal joining techniques such as discussed elsewhere herein, e.g., soldering, welding, swaging, or by use of a die.

FIG. 4B shows a cross section of the FIG. 4A a device. It is as clear that the joint is conical joint. The inner section (164) is surrounded by the outer tubing (166).

FIG. 5A shows another variation of inventive guidewire (170) having a joint region (172) between a distal and (174) of a super elastic alloy and a more proximal section (176) typically of a stainless steel to provide inherent stiffness in torque transmission to that proximal portion. In this instance, joint region (172) has an outer tubing (178) joining the two sections. This allows the flexibility of the guidewire to be more controlled and the transition between the distal end (174) and the proximal end (176) to be somewhat more gradual. The outer section of tubing (178) is typically stainless steel or super elastic alloy or the like. A nitinol or other super elastic alloy would be a good choice for coverings such as these (providing they can be soldered or welded to the metals in the underlying joint) so to provide a region of varying stiffness between the proximal portion (176) and the distal portion (174).

The way in which the joint is provided is of some interest. The more proximal section (176) is cut at an angle or bias to the axis of the wire and the more distal section (174) is further cut at that same angle to the axis. The two sections are co-joined and covered by tubing (178) of an appropriate material. This joint is somewhat easier to than the conical joint shown in FIG. 4A.

FIG. 5B shows a cross section of joint (172) depicting the outer joint covering (178), the distal section (174) (cut at an angle) and the distal section (176). Assembly of this device is quite simple. However, the joining techniques are typically critical. Firm joints between the various metals must be obtained lest the joint separate.

FIG. 6 shows another variation of the inventive guidewire (190) utilizing various aspects of the variations described above. In this variation, distal section (192) is solid and of course is constructed of a super elastic alloy. In this variation, the more proximal section (194) is a tubing member able to provide a superior torque transmittance and stiffness to the overall guidewire device. There is a significant overlap in joint area (196) between distal section (192) and proximal section (194). This provides for a fairly gradual stiffness transition between those two sections. In this variation, it is feasible to place polymers (198) within the hollow of proximal section (194). Polymers should preferably be of the type which provides some measure of adhesion to the interior of more proximal tube (194). In this way, the polymer materials are more than mere space fillers. If they adhere to the inner wall of tubing member (194), they will provide the catheter assembly with additional torque transmission capabilities. Even in the absence of adhesion between the polymer (198) and wire (198) we found it prevents some measure of kinking just due to the bulk found there. Suitable polymers are those that will flow through the modest opening in the hypotube making up more proximal section (194). Furthermore, should the polymer not be one which is adhesive to the metal, yet nevertheless prevents the guidewire from kicking or collapsing simply because of the bulk in the middle of the tubing (194).

Each of the variation shown in FIGS. 2 through 6 may have coils such as are shown in FIG. 1 on their distal tip. However, such is not necessary for the invention.

Materials for the guidewire tip are materials such as platinum, palladium, rhodium and the like.

We have found it desirable to coat all or part of the guidewire core (as will be discussed in more detail below) with a lubricious coating material such as polyfluorocarbons (e.g., Teflon) or with hydrophilic polymers. As is discussed below, when using hydrophilic polymers as the coating material, it is often desirable to use a tie layer on the guidewire core. The composition of such tie layers will be also discussed below.

Guidewire Core

This guidewire is typically used in a catheter which is made up of an elongate tubular member having proximal and distal ends. The catheter is (again) about 50 to 300 centimeters in length, typically between about 100 and 200 centimeters in length. Often, the catheter tubular member has a relatively stiff proximal section which extends along a major portion of the catheter length and one or more relatively flexible distal sections which provide greater ability of the catheter to track the guidewire through sharp bends and turns encountered as the catheter is advanced through the torturous paths found in the vasculature. The construction of a suitable catheter assembly having differential flexibility along its length is described in U.S. Pat. No. 4,739,768.

We have found that certain alloys, particularly Ni—Ti alloys, retain their super-elastic properties during traversal through the vasculature and yet are sufficiently pliable that they provide the physician using the guidewire with enhanced "feel" or feedback and yet do not "whip" during use. That is to say, as a guidewire is turned it stores energy during as a twist and releases it precipitously as it "whips" to quickly recover the stored stress. The preferred alloys do not incur significant unrecovered strain during use.

The material used in the guidewires of this invention are of shape memory alloys which exhibit super-elastic/pseudo-elastic shape recovery characteristics. These alloys are known. See, for instance, U.S. Pat. Nos. 3,174,851 and 3,351,463 as well as U.S. Pat. No. 3,753,700. These metals are characterized by their ability to be transformed from an austenitic crystal structure to a stress-induced martensitic (SIM) structure at certain temperatures, and return elastically to the austenitic structure when the stress is removed. These alternating crystalline structures provide the alloy with its super-elastic properties. One such well-known alloy, nitinol, is a nickel-titanium alloy. It is readily commercially available and undergoes the austenite-SIM-austenite transformation at a variety of temperature ranges between −20° C. and 30° C.

These alloys are especially suitable because of their capacity to elastically recover almost completely to the initial configuration once the stress is removed. Typically there is little plastic deformation, even at relatively high strains. This allows the guidewire to undertake substantial bends as it passes through the body's vasculature, and yet return to its original shape once the bend has been traversed without retaining any hint of a kink or a bend. However, the tips shown are often sufficiently plastic that the initial tip formation is retained. Nevertheless, compared to similar stainless steel guidewires, less force need be exerted against the interior walls of the vessels to deform the guidewire of the invention along the desired path through the blood vessel thereby decreasing trauma to the interior of the blood vessel and reducing friction against the coaxial catheter.

Guidewire Core Coatings

As mentioned above, all or part of the guidewire core may be covered or coated with one or more layers of a polymeric material. The coating is applied typically to enhance the lubricity of the guidewire core during its traversal of the catheter lumen or the vascular walls.

Coating Materials

As noted above, at least a portion of the guidewire core may simply be coated by dipping or spraying or by similar process with such materials as polysulfones, polyfluorocarbons (such as TEFLON), polyolefins such as polyethylene, polypropylene, polyesters (including polyamides such as the NYLON's), and polyurethanes; their blends and copolymers such as polyether block amides (e.g., PEBAX).

It is often desirable to utilize a coating such as discussed just above on the proximal portion of the guidewire and a coating such as discussed below on the more distal sections. Any mixture of coatings placed variously on the guidewire is acceptable as chosen for the task at hand.

The guidewire core may also be at least partially covered with other hydrophilic polymers including those made from monomers such as ethylene oxide and its higher homologs; 2-vinyl pyridine; N-vinylpyrrolidone; polyethylene glycol acrylates such as mono-alkoxy polyethylene glycol mono (meth)acrylates, including mono-methoxy triethylene glycol mono (meth)acrylate, mono-methoxy tetraethylene glycol mono (meth)acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The polymeric coating may be cross-linked using various techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Polymers or oligomers applied using the procedure described below are activated or functionalized with photoactive or radiation-active groups to permit reaction of the polymers or oligomers with the underlying polymeric surface.

Suitable activation groups include benzophenone, thioxanthone, and the like; acetophenone and its derivatives specified as:

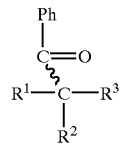

where
$R^1$ is H, $R^2$ is OH, $R^3$ is Ph; or
$R^1$ is H, $R^2$ is an alkoxy group including —OCH$_3$, —OC$_2$H$_3$, $R^3$ is Ph; or
$R^1=R^2=$an alkoxy group, $R^3$ is Ph; or
$R^1=R^2=$an alkoxy group, $R^3$ is H; or
$R^1=R^2=$Cl, $R^3$ is H or Cl.

Other known activators are suitable.

The polymeric coating may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric coating may be applied to the guidewire by any of a variety of methods, e.g., by spraying a solution or suspension of the polymers or of oligomers of the monomers onto the guidewire core or by dipping it into the solution or suspension. Initiators may be included in the solution or applied in a separate step. The guidewire may be sequentially or simultaneously dried to remove solvent after application of the polymer or oligomer to the guidewire and crosslinked.

The solution or suspension should be very dilute since only a very thin layer of polymer is to be applied. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

Particularly preferred as a coating for the guidewire cores discussed herein are physical mixtures of homo-oligomers of at least one of polyethylene oxide; poly 2-vinyl pyridine; polyvinylpyrrolidone, polyacrylic acid, polyacrylamide, and polyacrylonitrile. The guidewire bodies or substrates are preferably sprayed or dipped, dried, and irradiated to produce a polymerized and crosslinked polymeric skin of the noted oligomers.

The lubricious hydrophilic coating is preferably produced using generally simultaneous solvent removal and crosslinking operations. The coating is applied at a rate allowing "sheeting" of the solution, e.g., formation of a visibly smooth layer without "runs". In a dipping operation for use with most polymeric substrates including those noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 50° C. to 125° C. Most preferred for the noted and preferred solvent systems is the range of 75° to 110° C.

Ultraviolet light sources may be used to crosslink the polymer precursors onto the substrate. Movement through an irradiation chamber having an ultraviolet light source at 90–375 nm (preferably 300–350 nm) having an irradiation density of 50–300 mW/cm$^2$ (preferably 150–250 mW/cm$^2$) for a period of three to seven seconds is desired. Passage of a guidewire core through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

Tie Layers

We have found that it is often desirable to incorporate a "tie" layer as a coating between the outer polymeric surface and the guidewire core to enhance the overall adhesion of the outer polymeric surface to the core. Of course, these materials must be able to tolerate the various other solvents, cleaners, sterilization procedures, etc. to which the guidewire and its components are placed during other production steps.

Choice of materials for such tie layers is determined through their functionality. Specifically, the materials are chosen for their affinity or tenacity to the outer polymeric lubricious or hydrophilic coating. Clearly, the tie layer material must be flexible and strong. The tie layers may be placed onto the guidewire core in a variety of ways. The polymeric material may be extrudable and made into shrinkable tubing for mounting onto the guidewire through heating. It may be placed onto the guidewire core by dipping, spraying, shrink wrapping of polymeric tubing or other procedure. One quite desirable procedure involves the placement of a polymeric tubing of a fusible polymer, e.g., polyurethane, on the guidewire core which, in turn, is covered with a heat shrink tubing such as polyethylene. The outer tubing is shrunk down and the inner tubing is fused onto the guidewire core to form a tie layer. The tie layer is preferably 0.0004" to 0.003" in thickness. The melt temperature of the tie layer polymer desirably is appropriately chosen to fuse at the heat shrink temperature of the outer tubing. The outer shrink tubing is then simply peeled off, leaving the tie layer exposed for treatment with the lubricious coating.

We have found that various NYLON's, polyethylene, polystyrene, polyurethane, and polyethylene terephthalate (PET) make excellent tie layers.

Preferred are polyurethane (Shore 80A–55D) and PET. Most preferred is polyurethane. It is additionally desirable to use a number of sections of polyurethane having differing hardnesses. For instance, the distal section may have a tie layer of Shore 80A polyurethane; the proximal shaft might be Shore D55 polyurethane. These materials may be formulated or blended to include radio opaque materials such as barium sulfate, bismuth trioxide, bismuth carbonate, tungsten, tantalum or the like.

As noted above, another manner of applying a tie layer is by heat-shrinking the tubing onto the guidewire. The guidewire core is simply inserted into a tubing of suitable size. The tubing is cut to length and heated until it is sufficiently small in size. The resulting tubing tie layer desirably is between about 0.0005 and 0.015 inches in thickness. The thinner layers are typically produced from polyurethane or PET. The layer of lubricious polymer is then placed on the outer surface of the shrunk tubing.

Another procedure for preparing or pretreating guidewires prior to receiving a subsequent coating of a polymer, preferably a polymer which is lubricious, biocompatible, and hydrophilic, is via the use of a plasma stream to deposit a hydrocarbon or fluorocarbon residue. The procedure is described as follows: the guidewire core is placed in a plasma chamber and cleaned with an oxygen plasma etch. The guidewire core is then exposed to a hydrocarbon plasma to deposit a plasma-polymerized tie layer on the guidewire core to complete the pretreatment. The hydrocarbon plasma may comprise a lower molecular weight (or gaseous) alkanes such as methane, ethane, propane, isobutane, butane or the like; lower molecular weight alkenes such as ethene, propene, isobutene, butene or the like or; gaseous fluorocarbons such as tetrafluoromethane, trichlorofluoromethane, dichlorodifluoromethane, trifluorochloromethane, tetrafluoroethylene, trichlorofluoroethylene, dichlorodifluoroethylene, trifluorochloroethylene and other such materials. Mixtures of these materials are also acceptable. The tie layer apparently provides C—C bonds for subsequent covalent bonding to the outer hydrophilic polymer coating. Preferred flow rates for the hydrocarbon into the plasma chamber are in the range of 500 c.c./min. to 2000 c.c./min. and the residence time of the guidewire in the chamber is in the range of 1–20 minutes, depending on the chosen hydrocarbon and the plasma chamber operating parameters. Power settings for the plasma chamber are preferably in the range of 200 W to 1500 W.

A tie layer of plasma-produced hydrocarbon residue having a thickness on the order of 10$\mu$ thick is disposed between core and coating. This process typically produces layers of hydrocarbon residue less than about 1000$\mu$ in thickness, and more typically less than about 100$\mu$. Tie layer effectively bonds the outer layer to the guidewire core while adding very little additional bulk to the guidewire. Guidewires made according to this invention therefore avoid the size and maneuverability problems of prior art guidewires.

The pretreated guidewire may be coated by a polymer using a procedure such as described above. For example, the pretreated guidewire may be dipped in a solution of a photoactive hydrophilic polymer system, i.e., a latently photoreactive binder group covalently bonded to a hydrophilic polymer. After drying, the coated guidewire is cured by exposing it to UV light. The UV light activates the latently reactive group in the photoactive polymer system to form covalent bonds with crosslinked C—C bonds in the hydrocarbon residue tie layer. The dipping and curing steps are preferably repeated often enough, typically twice, to achieve the appropriate thickness of the hydrophilic coating layer.

One highly preferred variation of the invention involves a guidewire with metal core, preferably 0.010" to 0.025" diameter stainless steel or nitinol. The exterior surface of guidewire is a biocompatible coating of a polyacrylamide/polyvinylpyrrolidone mixture bonded to a photoactive binding agent.

The photoactive hydrophilic polymer system of this preferred embodiment is a mixture of a polyacrylamide and polyvinylpyrrolidone and provides both lubricity and binding for durability. The exact proportions of the two may be varied to suit the application. As an alternative, however, the hydrophilic biocompatible coating may be polyacrylamide alone, polyvinylpyrrolidone alone, polyethylene oxide, or any suitable coating known in the art. In addition, a coating of heparin, albumin or other proteins may deposited over the hydrophilic coating in a manner known in the art to provide additional biocompatibility features.

The guidewire or other device may be cleaned by using an argon plasma etch in place of the oxygen plasma etch. The thickness of the plasma-polymerized tie layer may also vary without departing from the scope of this invention.

Although preferred embodiments of the present invention have been described, it should be understood that various changes, adaptations, and modifications may be made therein without departing from the spirit of the invention and the scope of the claims which follow.

We claim as our invention:

1. A guidewire for guiding a catheter within a body lumen, comprising an elongated, flexible metal wire core having at least a more-proximal non-super elastic portion having a flexibility and a more-distal super-elastic alloy distal section having a flexibility and wherein the more proximal portion and the more distal section are separated by and joined with a mid section, at least a portion of which mid-section varies in flexibility and which flexibility lies in value between the flexibility of the more-proximal portion and the flexibility of the more-distal super-elastic alloy distal section so that the midsection provides a gradual transition in flexibility between the proximal portion and the distal region, and wherein at least the more-proximal portion comprises another material or configuration not included in the more-distal super-elastic alloy distal section.

2. The guidewire of claim 1 in which the super-elastic alloy comprises nickel and titanium.

3. The guide wire of claim 1 wherein the distal section is at least partially covered with a helically wound ribbon or coil.

4. The guidewire of claim 3 wherein the helically wound ribbon or coil comprises a metal material selected from super-elastic alloys or radio-opaque alloys.

5. The guidewire of claim 3 wherein the helically wound ribbon or coil comprises platinum.

6. The guidewire of claim 4 wherein the helically wound ribbon or coil comprises titanium and nickel.

7. The guidewire of claim 1 further comprising a tie layer situated exterior to at least a portion of the more-distal section or more-proximal section.

8. The guidewire of claim 7 where the tie layer comprises at least one of NYLON, polyethylene, polystyrene, polyurethane, and polyethylene terephthalate.

9. The guidewire of claim 7 where the tie layer comprises polyethylene terephthalate or polyurethane.

10. The guidewire of claim 9 wherein the tie layer is polyurethane and has a variable hardness distally.

11. The guidewire of claim 7 in which at least a portion of the polymeric tie layer is coated with a lubricious polymeric material.

12. The guidewire of claim 11 in which lubricious polymeric material comprises at least one hydrophilic polymer.

13. The guidewire of claim 7 where the tie layer additionally comprises a radio-opaque material selected from barium sulfate, bismuth trioxide, bismuth carbonate, tungsten, and tantalum.

14. The guidewire section of claim 1 additionally comprising a catheter sheath.

* * * * *